United States Patent
Serizawa et al.

(10) Patent No.: US 6,746,673 B2
(45) Date of Patent: Jun. 8, 2004

(54) PHARMACEUTICAL COMPOSITIONS CONTAINING ANTI-FAS ANTIBODY

(75) Inventors: Nobufusa Serizawa, deceased, late of Yokohama (JP), by Setsu Serizawa, legal representative; Kimihisa Ichikawa, Yokohama (JP); Hiroko Yoshida, Tokyo (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/989,620

(22) Filed: Nov. 20, 2001

(65) Prior Publication Data

US 2002/0103212 A1 Aug. 1, 2002

Related U.S. Application Data

(63) Continuation-in-part of application No. PCT/JP00/03324, filed on May 24, 2000.

(30) Foreign Application Priority Data

May 24, 1999 (JP) ............................................. 11-143033

(51) Int. Cl.$^7$ ...................... A61K 39/395; C07K 16/00; A01N 43/58
(52) U.S. Cl. ............................... 424/130.1; 424/133.1; 424/141.1; 514/2; 514/249; 530/387.1; 530/387.3; 530/388.1
(58) Field of Search ........................... 435/7.1; 530/324, 530/327, 360, 397.1, 389.23, 388.24; 536/28.1, 234; 514/253, 415, 249, 258; 544/279, 260; 424/130.1, 133.1, 141.1

(56) References Cited

U.S. PATENT DOCUMENTS

| 4,912,112 A | | 3/1990 | Seydel et al. | |
| 5,633,373 A | * | 5/1997 | Barnett et al. | 544/279 |
| 5,952,499 A | * | 9/1999 | Whittaker et al. | 544/260 |
| 6,001,962 A | * | 12/1999 | Ramer et al. | 530/324 |
| 6,004,942 A | * | 12/1999 | Firestein et al. | 514/44 |
| 6,098,631 A | * | 8/2000 | Holoshitz et al. | 128/898 |
| 6,153,615 A | * | 11/2000 | Gross | 514/254.09 |
| 6,221,615 B1 | * | 4/2001 | Chittenden et al. | 435/7.1 |
| 6,544,523 B1 | * | 4/2003 | Chu | 424/192.1 |

FOREIGN PATENT DOCUMENTS

| EP | 0 021 292 A1 | 1/1981 |
| EP | 0 334 636 A2 | 9/1989 |
| EP | 0 709 097 A1 | 5/1996 |
| EP | 0 866 131 A2 | 9/1998 |
| EP | 0 897 724 A1 | 2/1999 |
| EP | 0 909 816 A1 | 4/1999 |
| JP | 2-237935 A | 9/1990 |
| JP | 5-503281 A | 6/1993 |
| WO | WO 86/05181 A1 | 9/1986 |
| WO | WO 91/10448 A1 | 7/1991 |
| WO | WO 91/10666 A1 | 7/1991 |
| WO | WO 92/08461 A1 | 5/1992 |
| WO | WO 93/13079 A1 | 7/1993 |
| WO | WO 95/09845 A1 | 4/1995 |

OTHER PUBLICATIONS

Yonehara, International Reviews of Immunology, vol. 18, pp. 329–345 (1999).*
Signore et al., Diabetes/Metabolism Reviews, vol. 14, pp. 197–206 (1998).*
Rose et al., British Journal of Rheumatology, vol. 36, pp. 158–163 (1997).*
Defranco et al., Diabetes, vol. 50, pp. 483–488 (2001).*
Moulian et al., Blood, vol. 89, pp. 3287–3295 (1997).*
Eguchi, Internal Medicine, vol. 40, pp. 275–284 (2001).*
Yonehara, Cytokine and Growth Factor Reviews, vol. 13, pp. 393–402 (2002).*
Genestier et al. Journal of Clinical Investigation, vol. 102, pp. 322–328 (1998).*
Kerr et al., "Apoptosis: A Basic Biological phenomenon With Wide–Ranging Implications In Tissue Kinetics", *Br. J. Cancer*, 26, (1972), pp. 239–257.
Nakayama et al., "The Selection of T Cell and Apoptoss", *Mebio*, 12, (10), (1995), pp. 79–86.
Yonehara et al., "A Cell–Killing Monoclonal Antibody (Anti–Fas) To A Cell Surface Antigen Co–Downregulated With the Receptor of Tumor Necrosis Factor", *J. Exp. Med.*, 169, (1989), pp. 1747–1756.
Loetscher et al., "Molecular Cloning and Expression of the Human 55 kd Tumor Necrosis Factor Receptor", *Cell*, 61, (1990), pp. 351–359.
Tsubata et al., "B–Cell Apoptosis Induced by Antigen Receptor Crosslinking is Blocked by a T–Cell signal through CD40", *Nature*, 364, (1993), pp. 645–648.
Jenne et al., "Granzymes, a Family of Serine Proteases Released from Granules of Cytolytic T Lymphocytes upon T Cell Receptor Stimulation", *Immunological Reviews*, 103, (1988), pp. 53–71.
McCarty, "Arthritis And Allied Conditions", *A Textbook of Rheumatology*, 10$^{th}$ Edition (1985), Lea & Febiger, pp. xvii–xxii.
Nakajima et al., "Apoptosis And Functional Fas Antigen In Rheumatoid Arthritis Synoviocytes", *Arthritis & Rheumatism*, 38, (4), (1995), pp. 485–491.

(List continued on next page.)

*Primary Examiner*—James Housel
*Assistant Examiner*—Zachariah Lucas
(74) *Attorney, Agent, or Firm*—Frishauf, Holtz, Goodman & Chick, P.C.

(57) ABSTRACT

A pharmaceutical composition containing an anti-human Fas antibody having apoptosis inducing activity and a compound having a folate antagonist activity or a dihydrofolate reductase inhibiting activity, as active ingredients for the prophylaxis and/or treatment of an autoimmune disease or rheumatoid arthritis. According to the present invention, the amount of the anti-Fas antibody to be used can be reduced and thereby the possibility that a patient may become tolerant to anti-Fas antibody as a result of the production of antibodies against the anti-Fas antibody in the patient's body or the like can be decreased, and thus is provided a pharmaceutical composition which can be used for a long time.

14 Claims, 3 Drawing Sheets

OTHER PUBLICATIONS

Aono et al., "Inducing Apoptosis by Using Anti Fas Antibody Against Chronic Rheumatism Synovial Cells", *38th Japan Rheumatic Society Summary Collection*, (1994), p. 487.

Dao et al., "Relation of bcl–2 and c–myc expression to apoptosis in a human leukemia T cell line induced by natural human tumor necrosis factor– α", *Proceedings Of The Japanese Cancer Association, Japanese Journal of Cancer Research*, 53 Annual Meeting, Nagoya 1994, Hesei 6, p. 338.

Trauth et al., "Monoclonal Antibody–Mediated Tumor Regression by Induction of Apoptosis", *Science, 245*, (1989), pp. 301–305.

Kalden, "Anti–TNF–α and Other Treatment Principles for RA", *7th International Rheumatology Symposium in Kyoto*, (1998), pp. 12–13.

McGahon et al., "Chemotherapeutic Drug–Induced Apoptosis in Human Leukaemic Cells is Independent of the FAS (APO–1/CD95) Receptor/Ligand System", *British Journal of Haematology, 101*, (1998), pp. 539–547.

Mizutani et al., "Doxorubicin Sensitizes Human Bladder Carcinoma Cells to Fas–Mediated Cytotoxicity", *American Cancer Society, 79*, (6), (1997), pp. 1180–1189.

Serizawa, "Trials on the Development of Drug by an Novel Anti–Fas Monoclonal Antibody", *Saishin–igaku, 54*, (4), (1999), pp. 917–924.

"Edatrexate", *The Merck Index, 3553*, 12th Edition, (1996), pp. 592–593.

Mizutani et al., "Sensitization Of Human Bladder Cancer Cells to Fas–Mediated Cytotoxicity By Cis–Diamminedichloroplatinum", *J. of Urology, 160*, (2), (1998), pp. 561–571.

"Trimetrexate", *The Merck Index*, 12th Edition, 9851, (1996), p. 1656.

"Brodimoprim", *The Merck Index*, 12th Edition, 1401, (1996), p. 226.

Kotake et al., "Synthesis and Antitumor Activities of Novel 6–5 Fused Ring Heterocycle Antifolates: N–[4[ω(2–Amino–4–Substituted–6,7–Dihydrocyclopenta[d]pyrimidin–5–yl)alkyl]benxoyl]–L–glutamic Acids", *J. Med. Chem., 37*, (11), (1994), pp. 1616–1624.

Faessel et al., "Super in Vitro *Synergy* between Inhibitors of Dihydrofolate Reductase and Inhibitors of Other Folate–requiring Enzymes: The Critical Role of Polyglutamylation", *Cancer Research, 58*, (14), (1998), pp. 3036–3050.

Rosowsky et al., "Synthesis and Biological Activity of Methotrexate Analogues with Two Acid Groups and a Hydrophobic Aromatic Ring in the Side Chain", *J. Med. Chem., 34*, (2), (1991), pp. 574–579.

Hughes et al., "Anti–*Pneumocystis carinii* Activity of PS–15, a New Biguanide Folate Antagonist", *Antimicrobial Agents And Chemotherapy, 37*, (7), (1993), pp. 1417–1419.

Genestier et al., "Immunosuppressive Properties of Methotrexate: Apoptosis and Clonal Deletion of Activated Peripheral T Cells", *J. Clin. Invest., 102*, (2), (1998), pp. 322–328.

Nishimura–Morita et al, "Amelioration of Systemic Autoimmune Disease by the Stimulation of Apoptosis–Promoting Receptor Fas with Anti–Fas mAb", *International Immunology, 9* (12); (1997), pp. 1793–1799.

Fujisawa, "Anti–Fas mAb Therapy in Murine Arthritis", *Molecular Medicine, 33*, (11), (1996), pp. 1254–1261.

Fujisawa et al., "Therapeutic Effect of Anti–Fas Antibody on Arthritis in HTLV–I Tax Transgenic Mice", *J. Clin. Invest., 98*, (2), (1998), pp. 271–278.

Sakai et al., "Potential Withdrawal Of Rheumatoid Synovium By The Induction Of Apoptosis Using A Novel In Vivo Model Of Rheumatoid Arthritis", *Arthritis & Rheumatism, 41*, (7), (1998), pp. 1251–1257.

Hasunuma et al., "Induction of Fas–Dependent Apoptosis in Synovial Infiltrating Cells in Rheumatoid Arthritis", *Int. Imunol., 8*, (10), (1996), pp. 1595–1602.

Sumida et al., "Rheumatoid Arthritis and Apoptosis", *Intern. Med., 37*, (2), (1998), pp. 184–188.

\* cited by examiner

US 6,746,673 B2

PHARMACEUTICAL COMPOSITIONS CONTAINING ANTI-FAS ANTIBODY

This application is a continuation-in-part application of international application PCT/JP00/03324 filed May 24, 2000 (not published in English).

BACKGROUND OF THE INVENTION

1. Field of the Invention

The present invention relates to a novel pharmaceutical composition for prophylaxis and/or treatment of an autoimmune disease or rheumatoid arthritis.

2. Background Art

Physiological death of cells as a result of normal alternation of cells in a living organism is called apoptosis, and is distinguished from the pathological death of cells, i.e. necrosis [cf. Kerr et al., (1972), Br. J. Cancer, 26, 239]. Apoptosis is a kind of so-called programmed cell death, which is observed in certain cells that are programmed, in advance, to die in a living organism. Apoptosis is characterized by a curved cell surface, condensed nuclear chromatin and fragmented chromosomal DNA, amongst others.

Apoptosis plays a role in the differentiation of lymphocytes (T cells and B cells) by eliminating cells that recognize an autoantigen. It is believed that a cause of an autoimmune disease is the presence of auto-reactive lymphocytes generated due to failure of apoptosis in differentiation of lymphocytes [cf. Nakayama et al., (1995), Mebio, 12 (10), 79–86].

Various molecules have been identified as being involved in apoptosis, including: Fas [cf. Yonehara. S., et al., (1989), J. Exp. Med., 169, 1747–1756]; tumor necrosis factor receptor [cf. Loetscher. H., et al., (1990), Cell, 61, 351–359]; CD40 [cf. Tsubata, T., et al., (1993), Nature, 364, 645–648]; and perforin/granzyme A [cf. Jenne. D. E., et al., (1988), Immunol. Rev. 103, 53–71]. Fas is a transmembrane protein present on the cellular surface, and binding of its extracellular domain to a protein called the "Fas ligand" induces apoptosis in the cell.

It has been reported that some anti-Fas monoclonal antibodies have a cytotoxic activity and induce apoptosis in a cell in a similar manner as the Fas ligand does, and thus they can be an agent for treating an autoimmune disease, AIDS, and neoplasm [cf. Japanese Patent Application Publication (Kokai) Hei 2-237935 and International application publication in Japan (Kohyo) Hei 5-503281].

On the other hand, rheumatism, especially rheumatoid arthritis is a disease that is accompanied by various abnormalities in immunology caused by internal and external factors, of which a basic pathological change is proliferation of synovial cells, and it is considered that it is a disorder of proliferation of the synovial cells accompanied by inflammatory cell infiltration and bone erosion. Tissue destruction around the joint suffering from rheumatoid arthritis is considered to be caused by abnormalities in the production of cytokines in inflammatory synovial cells. When the state of a joint of a rheumatic patient is investigated, there are observed an unusual proliferation of synovial cells, synovial villus proliferation, multilayered synovial cells and the like (cf. Daniel J. McCarty (1985) in "Arthritis and allied conditions, A textbook of rheumatology" $10^{th}$ Edition, Lea & Febiger). An anti-inflammatory agent or an immunity regulatory agent, such as a steroid or the like is mainly used in pharmacotherapy that is presently carried out for rheumatism. However, if such excrescence of synovial cells can be controlled with a medicine, it is considered that such a medicine would be useful as an agent for treating rheumatism.

Incidentally, it is known that proliferation of the synovial cells in rheumatism is not out of control, but is spontaneously controlled (cf. Daniel J. McCarty (1985) in "Arthritis and allied conditions, A textbook of rheumatology" $10^{th}$ Edition, Lea & Febiger). Furthermore, it has become clear recently that apoptosis is caused in synovial cells of a rheumatic patient and that the Fas antigen appears on a membrane of the synovial cells. Nakajima et al. (cf. Nakajima, T., et al. (1995) Arthritis Rheum. 38, 485–491) and Aono et al. (cf. 38th Japan rheumatic society summary collection (1994), 487 page and Heisei 6 Japan cancer society general meeting reports 1994, 338 page) have studied whether apoptosis is induced in a synovial cell when the anti-human Fas antibody having a cytotoxic activity is added to the abnormally proliferating synovial cells originated from a rheumatic patient, and have found that apoptosis is induced at a higher rate in the abnormally proliferating synovial cells originated from a rheumatic patient, than in synovial cells which are not originated from a rheumatic patient. Accordingly, an anti-human Fas antibody can selectively induce apoptosis, not only in a lymphocyte, but also in the abnormally proliferating synovial cells, and therefore it is considered to be useful as an agent for rheumatism.

Several kinds of anti-human Fas mouse monoclonal antibodies have already been found (cf. Yonehara, S., et al (1989) J. Exp. Med. 1, 1747–1756, (1989); SCIENCE, 245, 301–305 (1989), and the like). Furthermore, as described above, it has been reported that the antibodies induce apoptosis in synovial cells of a rheumatic patient, in-vitro (cf. 38th Japan rheumatic society summary collection (1994), p.487; and Japan cancer society general meeting reports (1994), p.338). Furthermore, some anti-Fas antibodies have been found to be effective and safe for treatment in an autoimmune disease model animal or a rheumatoid arthritis model animal (cf. European patent application publication No. 0909816).

On the other hand, it is known that the effect of treatment for a rheumatoid arthritis patient can be increased by using methotrexate and a monoclonal antibody cA2 against a tumor necrosis factor α (TNFα) together (Carden, the 7th international rheumatism symposium summary (1998) p.12–13). However, a synergistic effect of an anti-Fas antibody and methotrexate was not heretofore known at all.

If there is a compound which reinforces the efficacy of an anti-Fas antibody useful as an agent for the prophylaxis and/or treatment of an autoimmune disease or rheumatoid arthritis, the amount of the anti-Fas antibody to be used can be decreased by using the compound and an anti-Fas antibody together. Thereby, the possibility that a patient becomes tolerant to an anti-Fas antibody as a result of production of antibodies against anti-Fas antibodies in the patient's body or the like can be decreased. Accordingly, there has been a need for a prophylactic or therapeutic agent consisting of a combination of an anti-Fas antibody and a compound reinforcing the efficacy of the anti-Fas antibody, which can be used for a long time.

The "synergy effect" shown in this application means a coordinated or correlated action by an anti-human Fas antibody and a compound having a folate antagonistic activity or dihydrofolate reductase inhibiting activity. The coordinated or correlated action is far stronger than would be expected by a person of ordinary skill in the art.

SUMMARY OF THE INVENTION

The present invention relates to a pharmaceutical composition comprising an anti-human Fas antibody having an apoptosis inducing activity and a compound having a folate antagonist activity or a dihydrofolate reductase inhibiting activity, as active ingredients. Preferably, the anti-human Fas antibody is a monoclonal antibody CH11, anti-human Fas monoclonal antibody HFE7A produced by a mouse-mouse hybridoma HFE7A (FERM BP-5828), or humanized antibodies thereof. Preferably, the above-mentioned compound having a folate antagonist activity or a dihydrofolate reductase inhibiting activity is selected from the group consisting of: methotrexate, edatrexate, epiroprim, iometrexol, pyritrexim, trimetrexate, brodimoprim, MX-68, N-[4-[3-(2,4-diamino-6,7-dihydro-5H-cyclopenta[d]pyrimidin-5-yl)propyl]benzoyl]-L-glutamic acid, N-[[5-[2-(2-amino-1,4,5,6,7,8-hexahydro-4-oxopyrido[2,3-d]-pyrimidin-6-yl)ethyl]-2-thienyl]carbonyl]-L-glutamic acid, (R)-N-[[5-[2-(2-amino-1,4,5,6,7,8-hexahydro-4-oxopyrido[2,3-d]pyrimidin-6-yl)ethyl]-2-thienyl]carbonyl]-L-glutamic acid, N-((2,4-diamino-3,4,5,6,7,8-hexahydropyrido[2,3-d]pyrimidin-6-yl)-ethyl)-2-thienylcarbonyl-L-glutamic acid, (S)-2-[[[4-carboxy-4-[[4-[[(2,4-diamino-6-pteridinyl)methyl]amino]benzoyl]amino]butyl]amino]carbonyl]benzoic acid, N-[4-[3-(2,4-diamino-1H-pyrrolo[2,3-d]pyrimidin-5-yl)propyl]benzoyl]-L-glutamic acid, 2,4-diamino-6-(N-(4-(phenylsulfonyl)benzyl)methylamino)quinazoline, 2,4-diamino-5-[4-[3-(4-aminophenyl-4-sulfonylphenylamino)propoxy]-3,5-dimethoxybenzyl]-pyrimidine, N-[4-[4-(2,4-diamino-5-pyrimidinyl)butyl]benzoyl]-L-glutamic acid, N-[4-[3-(2,4-diamino-5-pyrimidinyl)propyl]benzoyl]-L-glutamic acid, N-[4-[2-(2,4-diamino-6-pteridinyl)ethyl]benzoyl]-4-methylene-DL-glutamic acid and N-(1-methylethyl)-N'[3-(2,4,5-trichlorophenoxy)propoxy]imidodicarbonimidic diamide hydrochloride (PS15). Among them, methotrexate is the most preferable. The inventors of the present invention have found that the efficacy of the anti-Fas monoclonal antibody having an apoptosis inducing effect can be increased by using it together with a compound having a folate antagonist activity or a dihydrofolate reductase inhibiting activity, and thereby have completed the present invention.

As used herein, the term "an apoptosis inducing activity" means an activity of inducing apoptosis in a cell expressing Fas on a cell membrane surface by binding to the Fas.

The anti-human Fas antibody used as the first active ingredient of the pharmaceutical composition of the present invention may be one of those that can be specifically bound to human Fas and has an apoptosis inducing effect. Preferable examples of such an anti-human Fas antibody include: anti-human Fas monoclonal antibody CH11 and anti-human Fas monoclonal antibody HFE7A produced by the mouse-mouse hybridoma HFE7A (FERM BP-5828), or humanized antibodies thereof (European patent application publication No. 0909816), but the present invention is not limited thereto. In addition, the anti-human Fas monoclonal antibody of the present invention also includes recombinants of these anti-human Fas monoclonal antibodies, which have an effect equivalent to these monoclonal antibodies. Moreover, in the present invention, there can also be used a so-called humanized antibody modified using a gene recombination technology so that the immunogenicity to humans may be reduced, without deteriorating the binding ability of the above-mentioned anti-Fas monoclonal antibody to bind to Fas and its apoptosis inducing activity.

As used herein, the term "the compound having a folate antagonist activity or a dihydrofolate reductase inhibiting activity" means a pharmaceutically acceptable compound which has an activity of antagonistically inhibiting metabolism of the folic acid that is an indispensable process in synthesis of DNA in a cell. Preferable examples of such a compound include:

Methotrexate (the following formula (I)):

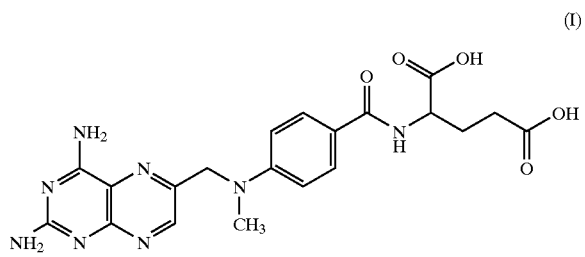

Edatrexate (cf. British patent publication No. GB 2058770 B, the following formula (II)):

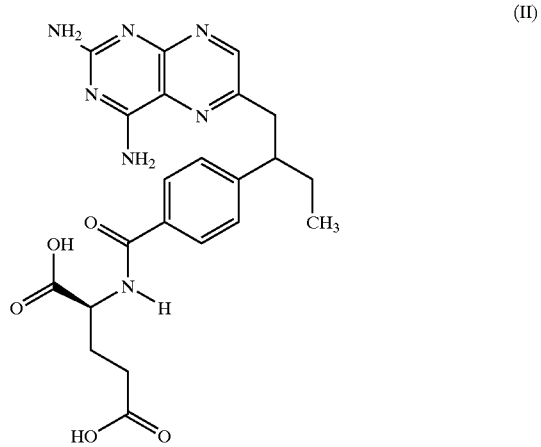

Epiroprim (cf. International patent application publication No. WO92/8461, the following formula (III)):

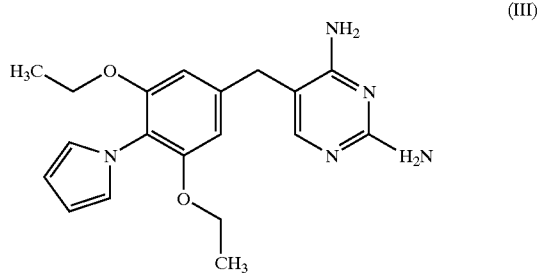

Iometrexol (cf. International patent application publication No. WO86/5181 publication, the following formula (IV)):

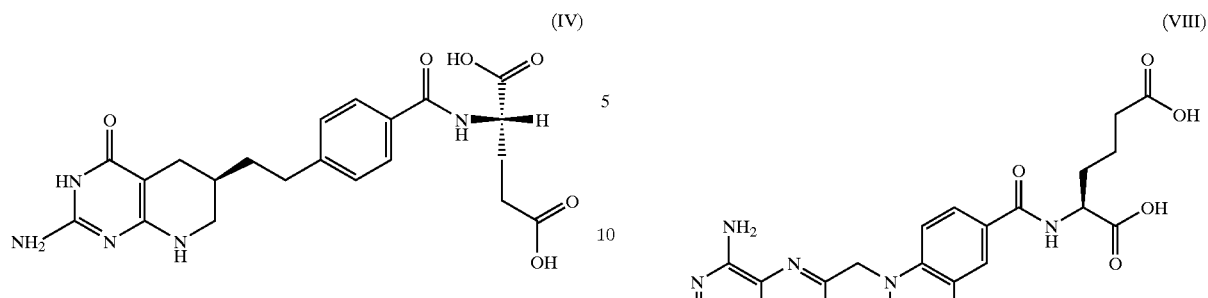

Pyritrexim (cf. European patent publication No. 21292, the following formula (V)):

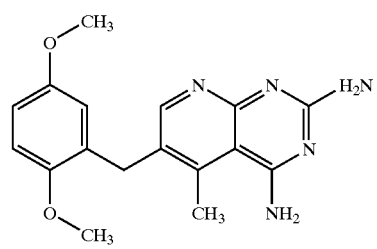

Trimetrexate (cf. British patent publication No. GB 1345502, the following formula (VI)):

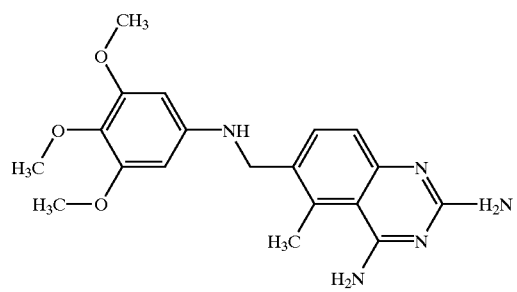

Brodimoprim (cf. British patent publication No. GB 1449387, the following formula (VII)):

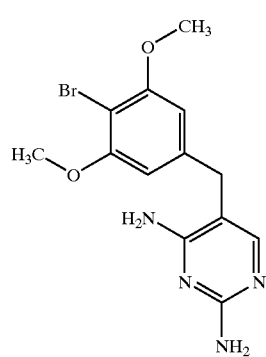

MX-68 (International patent application publication No. WO97/34606, the following formula (VIII)):

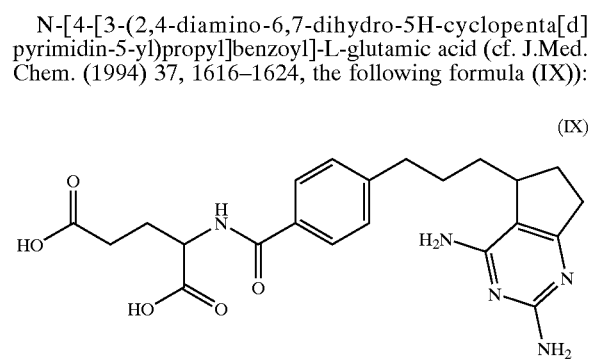

N-[4-[3-(2,4-diamino-6,7-dihydro-5H-cyclopenta[d]pyrimidin-5-yl)propyl]benzoyl]-L-glutamic acid (cf. J.Med. Chem. (1994) 37, 1616–1624, the following formula (IX)):

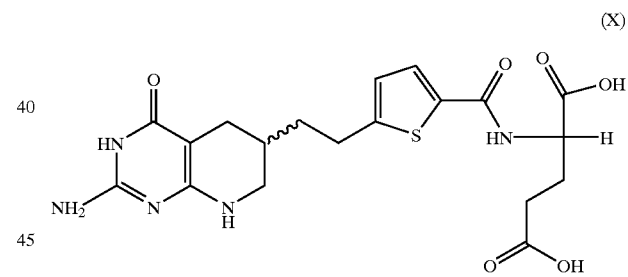

N-[[5-[2-(2-amino-1,4,5,6,7,8-hexahydro-4-oxopyrido[2,3-d]pyrimidin-6-yl)ethyl]-2-thienyl]carbonyl]-L-glutamic acid
(cf. European patent publication No. 343801, the following formula (X)):

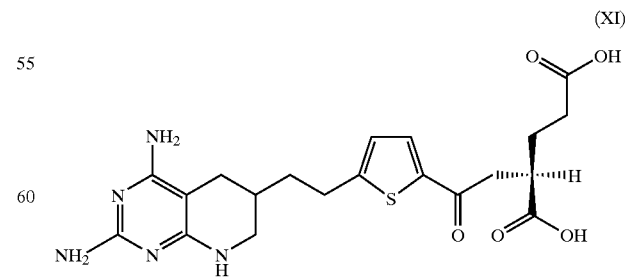

N-((2,4-diamino-3,4,5,6,7,8-hexahydropyrido[2,3-d]pyrimidin-6-yl)ethyl)-2-thienylcarbonyl-L-glutamic acid
(cf. Summary of U.S. cancer research society, 88th annual convention (1997) No. 660, the following formula (XI)):

(S)-2-[[[4-carboxy-4-[[4-[[(2,4-diamino-6-pteridinyl)methyl]amino]benzoyl]amino]-butyl]amino]carbonyl]benzoic acid (cf. European patent publication No. 345308, the following formula (XII)):

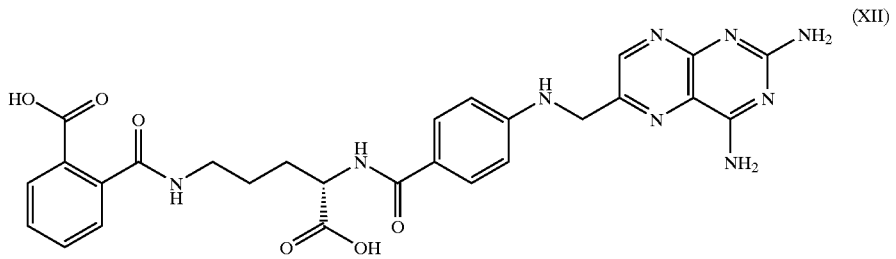

N-[4-[3-(2,4-diamino-1H-pyrrolo[2,3-d]pyrimidin-5-yl) propyl]benzoyl]-L-glutamic acid (cf. European patent publication No. 334636, the following formula (XIII)):

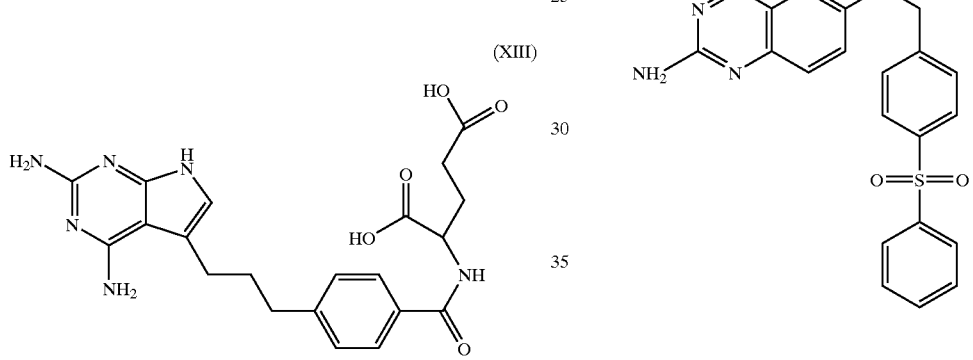

2,4-diamino-6-(N-(4-(phenylsulfonyl)benzyl) methylamino)quinazoline (cf. Summary of U.S. cancer research society, annual convention (1992) No. 2458, the following formula (XIV)):

2,4-diamino-5-[4-[3-(4-aminophenyl-4-sulfonylphenylamino)propoxy]-3,5-dimethoxybenzyl] pyrimidine (cf. European patent publication No. 231888, the following formula (XV)):

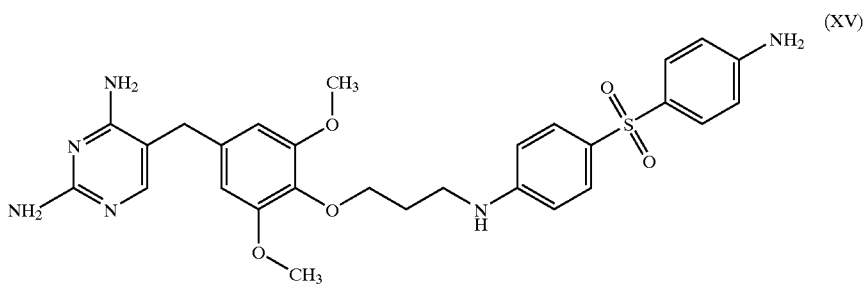

N-[4-[4-(2,4-diamino-5-pyrimidinyl)butyl]benzoyl]-L-glutamic acid (cf. International Patent Application No. WO95/9845, the following formula (XVI)):

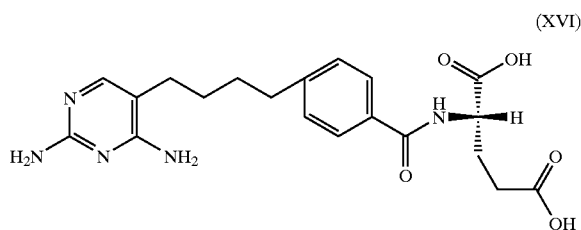

(XVI)

N-[4-[3-(2,4-diamino-5-pyrimidinyl)propyl]benzoyl]-L-glutamic acid (cf. International Patent Application No. WO95/9845, the following formula (XVII)):

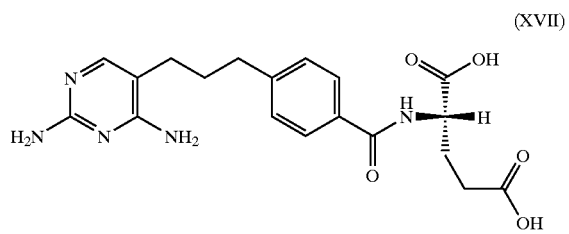

(XVII)

N-[4-[2-(2,4-diamino-6-pteridinyl)ethyl]benzoyl]-4-methylene-DL-glutamic acid (cf. International Patent Application No. WO91/10666, the following formula (XVIII)):

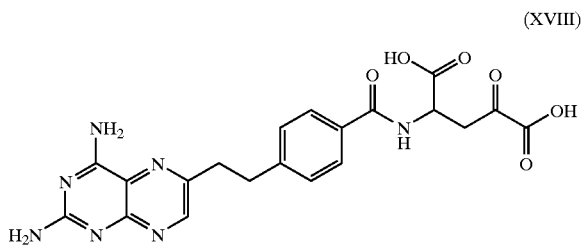

(XVIII)

N-(1-methylethyl)-N-[3-(2,4,5-trichlorophenoxy)propoxy]imidodicarbonimidic diamide hydrochloride (PS15) (cf. International Patent Application No. WO93/16037, the following formula (XIX)):

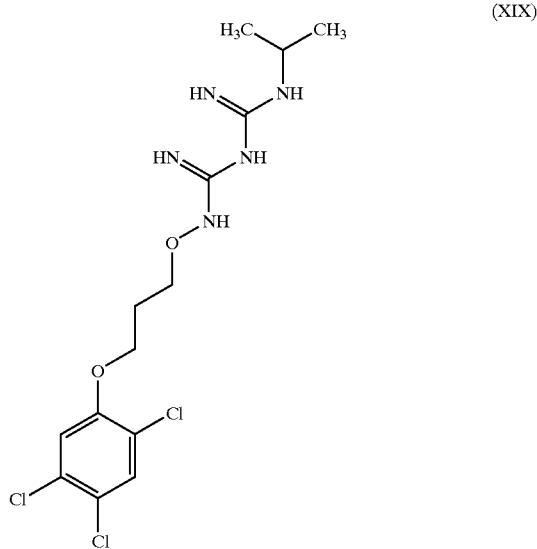

(XIX)

It is known that all of these compounds have a folate antagonist activity or a dihydrofolate reductase inhibiting activity. Among the above-mentioned compounds, methotrexate is the most preferable as the compound that is to be contained in the pharmaceutical composition of the present invention.

The pharmaceutical composition of the present invention can be obtained by formulating an appropriate mixture of an anti-Fas monoclonal antibody having an activity of inducing apoptosis in cells expressing Fas and a compound having a folate antagonist activity or a dihydrofolate reductase inhibiting activity.

The anti-Fas monoclonal antibody can be produced by methods known in the art using, for example, a molecule containing an extracellular domain of human Fas as an antigen. For example, the monoclonal antibody HFE7A that is one of the preferable anti-Fas monoclonal antibodies to be contained in the pharmaceutical composition of the present invention can be obtained by immunizing a Fas knock-out mouse with human Fas, subsequently fusing the spleen cells from the mouse with mouse myeloma cells, and culturing the resultant hybridoma. Specifically, it can be obtained according to the following method.

Preparation of a monoclonal antibody involves at least the following steps:

(a) purification of a biomacromolecule for use as the antigen;
(b) preparation of antibody producing cells, after immunizing an animal using injections of the antigen, bleeding the animal and assaying the antibody titer, in order to determine when to remove the spleen;
(c) preparation of myeloma cells;
(d) fusing the antibody producing cells and myeloma cells;
(e) selecting a hybridoma producing an antibody of interest;
(f) preparing a single cell clone (cloning);
(g) optionally, culturing the hybridoma cells, or growing animals into which the hybridoma cells have been transplanted, for large scale preparation of the monoclonal antibody; and
(h) testing the biological activities and the specificity, or assaying marker agent properties, of the monoclonal antibody thus prepared.

The method for the preparation of an anti-Fas monoclonal antibody is described below more in detail, in line with the above described steps. However, the method for preparing the antibody is not limited thereto. Other antibody producing cells than spleen cells and myeloma can also be used.

(a) Purification of Antigen

A recombinant protein (hereinafter referred to as "recombinant human Fas"), effective as the antigen, can be obtained by transfecting the monkey cell line COS-1 with the expression vector phFAS-AIC2, which encodes a fusion protein comprising the extracellular domain of human Fas and the extracellular domain of the mouse interleukin-3 receptor (hereinafter referred to as IL3R), [cf. Nishimura, Y., et al., (1995), J. Immunol., 154, 4395–4403] to express it, and collecting and partially purifying the expression product. The plasmid phFas-AIC2 was constructed by inserting DNA encoding a human Fas and mouse IL3R fusion protein into pME18S, which is an expression vector for animal cells. As noted above, the materials used, such as the DNA encoding Fas, the vector and the host, are not restricted to those mentioned.

For example, the human Fas and mounse IL3R fusion protein produced in the culture supernatant of the transformed COS-1 cells transfected with the plasmid phFas-AIC2 may be partially purified by ion-exchange chromatography using a Resource Q column (tradename; manufactured by Pharmacia).

Purified Fas obtained from the cell membranes of human cell lines can also be used as the antigen. Furthermore, since the primary structure of Fas is known [cf. Itoh, N., et al., (1991), Cell, 66, 233–243], a peptide comprising the known amino acid sequence may be chemically synthesized by a method well known in the art, and used as the antigen.

(b) Preparation of Antibody Producing Cells

The immunogen produced in step (a) is mixed with an adjuvant, such as Freund's complete or incomplete adjuvant and alum, and an experimental animal is immunized therewith. A suitable experimental animal may be a Fas knockout mouse, which may be produced by the method of Senju et al. [Senju, S., et al., (1996), International Immunology, 8, 423].

Suitable administration routes to immunize the mouse include the subcutaneous, intraperitoneal, intravenous, intradermal and intramuscular injection routes, with subcutaneous and intraperitoneal injections being preferred.

Immunization can be by a single dose or, by several repeated doses at appropriate intervals (preferably 1 to 5 weeks). Immunized animals are monitored for antibody titer in their sera, and an animal with a sufficiently high antibody titer is selected as the source of antibody producing cells. Selecting an animal with a high titer makes the subsequent process more efficient. Cells for the subsequent fusion are generally harvested from the animal 3 to 5 days after the final immunization.

Methods for assaying antibody titer include various well known techniques such as radioimmunoassay (hereinafter, referred to as RIA), solid-phase enzyme immunoassay (hereinafter, referred to as ELISA), fluorescent antibody assay and passive hemagglutination assay, with RIA and ELISA preferred for reasons of detection sensitivity, rapidity, accuracy and potential for automation.

Determination of antibody titer may be performed, for example, by ELISA, as follows. First, purified or partially purified Fas is adsorbed onto the surface of a solid phase, such as a 96-well ELISA plate, followed by blocking any remaining surface, to which Fas has not been bound, with a protein unrelated to the antigen, such as bovine serum albumin (hereinafter referred to as BSA). After washing, the well surfaces are contacted with serially diluted samples of the first antibody (for example, mouse serum) to enable binding of the anti-Fas antibody in the samples to the antigen. An enzyme-labeled, anti-mouse antibody, as the secondary antibody, is added to be bound to the mouse antibody. After washing, the substrate for the enzyme is added, and antibody titer can then be estimated by determining absorbance change due to color development caused by the decomposed substrate or the like.

(c) Preparation of Myeloma Cells

In general, cells from established mouse cell lines serve as the source of myeloma cells, for example, 8-azaguanine resistant mouse (derived from BALB/c) myeloma strains P3X63Ag8U.1 (P3-U1) [Yelton, D. E., et al., Current Topics in Microbiology and Immunology, 81, 1–7, (1978)], P3/NSI/1-Ag4-1(NS-1) [Kohler, G., et al., European J. Immunology, 6, 511–519 (1976)], Sp2/0-Ag14 (SP-2) [Shulman, M., et al., Nature, 276, 269–270 (1978)], P3X63Ag8.653 (653) [Kearney, J. F., et al., J. Immunology, 123, 1548–1550 (1979)] and P3X63Ag8 (X63) [Horibata, K. and Harris, A. W., Nature, 256, 495–497 (1975)]. The cell line selected is subcultured in an appropriate medium, such as 8-azaguanine medium [RPMI-1640 medium supplemented with glutamine, 2-mercaptoethanol, gentamicin, fetal calf serum (hereinafter referred to as FCS), and 8-azaguanine], Iscove's Modified Dulbecco's Medium (hereinafter referred to as IMDM) or Dulbecco's Modified Eagle Medium (hereinafter referred to as DMEM). The cells are then subcultured in a normal medium, such as ASF104 medium (Ajinomoto, K. K.) containing 10% FCS, 3 to 4 days prior to fusion, in order to ensure that at least $2 \times 10^7$ cells are available on the day of fusion.

(d) Cell Fusion

The antibody producing cells to be used are plasma cells and lymphocytes which are their precursor cells, which may be obtained from any suitable part of the animal. Typical areas are spleen, lymph nodes, peripheral blood, or any appropriate combination thereof, spleen cells most commonly being used.

After the last booster injection, tissue in which antibody producing cells are present, such as the spleen, is enucleated from a mouse having the predetermined antibody titer to prepare antibody producing cells such as spleen cells. The currently favored technique for fusion of the spleen cells with the myeloma cells prepared in step (c), employs polyethylene glycol, which has relatively low cytotoxicity and the fusion procedure using it is simple. An example of this technique is as follows.

The spleen and myeloma cells are washed well with serum-free medium (such as RPMI 1640) or phosphate buffered saline (hereinafter referred to as PBS) and then mixed, so that the number ratio of spleen cells to myeloma cells is approximately between 5:1 and 10:1, and then centrifuged. After the supernatant has been discarded and the pelleted cells sufficiently loosened, 1 ml of serum-free medium containing 50% (w/v) polyethylene glycol (m.w. 1,000 to 4,000) is added dropwise with stirring. Subsequently, 10 ml of serum-free medium is slowly added and then the mixture centrifuged. The supernatant is discarded again, and the pelleted cells are suspended in an appropriate amount of HAT medium containing a solution of hypoxanthin, aminopterin and thymidine (hereinafter referred to as "HAT") and mouse interleukin-2 (hereinafter referred to as IL-2). The suspension is then dispensed into the wells of culture plates (hereinafter referred to as "plates") and incubated in the presence of 5% v/v $CO_2$ at 37° C. for about 2 weeks, with the supplementary addition of HAT medium as appropriate.

(e) Selection of Hybridomas

When the myeloma strain used is resistant to 8-azaguanine, i.e., it is deficient in the hypoxanthin guanine phosphoribosyl transferase (HGPRT) enzyme, any unfused myeloma cells and any myeloma—myeloma fusions are unable to survive in HAT medium. On the other hand, fusions of antibody producing cells with each other, as well as hybridomas of antibody producing cells with myeloma cells can survive, the former only having a limited life. Accordingly, continued incubation in HAT medium results in selection of only the desired hybridomas.

The resulting hybridomas grown up into colonies are then transferred into HAT medium without aminopterin (hereinafter referred to as "HT medium"). Thereafter, aliquots of the culture supernatant are collected to determine anti-Fas antibody titer by, for example, ELISA. When the above-mentioned fusion protein is used as the ELISA antigen, it is also necessary to eliminate clones producing an antibody which specifically binds to the extracellular domain of the mouse IL3 receptor. The presence or absence of such a clone may be verified, for example, by ELISA using the mouse IL3 receptor, or its extracellular domain, as the antigen.

Although the above selection procedure is exemplified using an 8-azaguanine resistant cell line, it will be appreciated that other cell lines may be used with appropriate modifications to the media used.

(f) Cloning

Hybridomas which have been shown to produce specific antibodies, using a method similar to that described in the step (b) to determine antibody titer, are then transferred to another plate for cloning. Suitable cloning methods include: the limiting dilution method, in which hybridomas are diluted to contain one cell per well of a plate and then cultured; the soft agar method in which colonies are recovered after culturing in soft agar medium; a method of using a micromanipulator to separate a single cell for culture; and "sort-a-clone", in which single cells are separated by a cell sorter. Limiting dilution is generally the most simple and is commonly used.

The cloning procedure according to, for example, the limiting dilution method is repeated 2 to 4 times for each well demonstrating an antibody titer, and clones having stable antibody titers are selected as anti-Fas monoclonal antibody producing hybridomas. Hybridomas producing an anti mouse Fas antibody are selected by a similar method to obtain an anti-Fas monoclonal antibody producing cell line. A mouse Fas useful for this purpose, for example, is the fusion protein expressed by culturing animal cells transfected with the expression vector pME18S-mFas-AIC. This plasmid has DNA encoding a fusion protein comprising the extracellular domain of mouse Fas and the extracellular domain of the mouse IL3 receptor [cf. Nishimura. Y., et al., (1995). J. Immunol., 154, 4395–4403]. Other sources of murine Fas include purified mouse Fas and cells which express mouse Fas on their surface.

The mouse-mouse hybridoma HFE7A that produces the anti-Fas monoclonal antibody preferable as an active ingredient in the pharmaceutical composition of the present invention was deposited with the National Institute of Bioscience and Human-Technology at 1–3, Higashi 1-chome, Tsukuba, Ibaraki, Japan on Feb. 19, 1997, in accordance with the Budapest Treaty on the Deposition of Microorganisms, and was accorded the accession number FERM BP-5828. Accordingly, when preparing an antibody using the mouse-mouse hybridoma HFE7A, the preparation may be performed by following a procedure starting from the step (g) below, with the steps (a) to (f) omitted.

(g) Culture of Hybridoma to Prepare Monoclonal Antibody

The hybridoma obtained by the cloning is then cultured in normal medium, not in HT medium. Large-scale culture can be performed by roller bottle culture, using large culture bottles, or by spinner culture. The supernatant from the large-scale culture is purified by a suitable method, such as gel filtration, which is well known to those skilled in the art, to obtain an anti-Fas monoclonal antibody which the prophylactic or therapeutic agent of the present invention contains. The hybridoma may also be grown intraperitoneally in a syngeneic mouse, such as a BALB/c mouse or a Nu/Nu mouse, to obtain a large quantity of ascites containing an anti-Fas monoclonal antibody which the prophylactic or therapeutic agent of the present invention contains. Purification can also be conducted through use of commercially available monoclonal antibody purification kits (for example, MAbTrap GII Kit; Pharmacia).

Monoclonal antibodies prepared as above have a high specificity to human and mouse Fas.

(h) Assay of Monoclonal Antibody

Determination of the isotype and the subclass of the monoclonal antibody thus obtained may be performed as follows. Suitable identification methods include the Ouchterlony method, ELISA and RIA. The Ouchterlony method is simple, but requires concentration of the solution when the concentration of the monoclonal antibody is low. When ELISA or RIA is used, the culture supernatant can be reacted directly with an antigen adsorbed on a solid phase and with secondary antibodies having specificities for the various immunoglobulin isotypes and subclasses to identify the isotype and subclass of the monoclonal antibody. A method of using a commercial kit for identification, such as a Mouse Typer Kit (manufactured by Bio-Rad Laboratories, Inc.) is more simple.

Quantification of protein may be performed by the Folin-Lowry method, or by calculation based on the absorbance at 280 nm [1.4 (OD 280)=Immunoglobulin 1 mg/ml].

DNA encoding the heavy and light chains of the anti-Fas monoclonal antibody that is preferable as an active ingredient in the pharmaceutical composition of the present invention, may be obtained by preparing mRNA from hybridoma cells producing the anti-Fas monoclonal antibody, converting the mRNA into cDNA with reverse transcriptase, and then isolating the DNA encoding the heavy and/or light chains of the antibody, respectively.

Extraction of mRNA can be performed by the guanidinium thiocyanate-hot phenol method, the guanidinium thiocyanate-guanidinium HCl method, or the like, but the guanidinium thiocyanate-cesium chloride method is preferred. Preparation of mRNA from cells is generally performed by first preparing total RNA and then purifying mRNA from the total RNA by using a poly(A)$^+$ RNA purification matrix, such as oligo(dT) cellulose and oligo (dT) latex beads. Alternatively, mRNA may be prepared directly from a cell lysate using such a matrix. Methods for preparing total RNA include: alkaline sucrose density gradient centrifugation [cf. Dougherty, W. G. and Hiebert, E. (1980), Viology, 101, 466–474]; the guanidinium thiocyanate-phenol method; the guanidinium thiocyanate-trifluorocesium method; and the phenol-SDS method. The method using guanidinium thiocyanate and cesium chloride [cf. Chirgwin, J. M., et al., (1979), Biochemistry, 18, 5294–5299] is preferable.

The thus obtained poly(A)$^+$ RNA can be used as the template in a reverse transcriptase reaction to prepare single-strand cDNA which can then be converted to double stranded cDNA. Suitable methods therefor include the S1 nuclease method [cf. Efstratiadis. A., et al., (1976), Cell, 7, 279–288], the Gubler-Hoffman method [cf. Gubler. U. and Hoffman, B. J., (1983), Gene, 25, 263–269] and the Okayama-Berg method [cf. Okayama. H. and Berg, P., (1982). Mol. Cell. Biol., 2, 161–170]. However, the preferred method involves the polymerase chain reaction [hereinafter referred to as PCR, cf. Saiki, R. K., et al., (1988), Science, 239, 487–49] using single-strand cDNA as the template, namely "RT PCR".

The double-strand cDNA obtained above may then be integrated into a cloning vector and the resulting recombinant vector can then be used to transform a micro-organism, such as E. coli. The transformant can be selected using tetracycline resistance or ampicillin resistance. If E. coli is used, then transformation may be effected by the Hanahan method [cf. Hanahan, D., (1983), J. Mol. Biol., 166, 557–580]. Namely, the recombinant vector may be introduced into competent cells prepared by co-exposure to calcium chloride, magnesium chloride or rubidium chloride. If a plasmid is used as a vector, it is necessary that the plasmid harbors a drug-resistant gene, such as mentioned above. It is also possible to use other cloning vehicles, such as lambda phages.

In order to select transformants for those which carry cDNA encoding a subunit of an anti-Fas antibody of interest, various methods, such as those described below, can be used. When the cDNA of interest is specifically amplified by the above-mentioned RT-PCR, these steps may be omitted.

(1) Method by Polymerase Chain Reaction

If all or part of the amino acid sequence of the desired protein has been elucidated, then sense and antisense oligonucleotide primers corresponding to parts of the amino acid sequence can be synthesized, and used in the polymerase chain reaction technique [cf. Saiki, R. K., et al. (1988), Science, 239, 487–49] to amplify the desired DNA fragment encoding the anti-human Fas monoclonal antibody light chain subunit and heavy chain subunit. The template DNA may be, for example, cDNA synthesized by reverse transcription from mRNA of the hybridoma producing the anti-human Fas monoclonal antibody HFE7A (FERM BP-5828).

The DNA fragment thus synthesized may either be directly integrated into a plasmid vector by using a commercially available kit or the like, or may be labelled with, for example, $^{32}P$, $^{35}S$ or biotin, and then used as a probe for colony hybridization or plaque hybridization to obtain the desired clone.

Anti-Fas monoclonal antibody HFE7A that is preferable as an active ingredient in the pharmaceutical composition of the present invention is immunoglobulin GI (hereinafter referred to as "IgGI") comprising a heavy chain (γ1 chain) subunit and a light chain (K chain) subunit. The partial amino acid sequence of each of subunits mentioned above can be determined preferably by isolating each subunit by a well known method such as electrophoresis and column chromatography, and sequencing the N-terminal amino acid sequence of each subunit with an auto protein sequencer (for example, PPSQ-10 by Shimadzu Seisakusho, Corp.).

Harvesting of cDNA encoding each subunit of anti-human Fas monoclonal antibody from the appropriate transformants obtained above may be performed by well known techniques [cf. Maniatis, T., et al., in "Molecular Cloning A Laboratory Manual", Cold Spring Harbor Laboratory, NY, (1982)]. For example, the region of DNA encoding the desired subunit may be excised from plasmid DNA after separating the fraction corresponding to the vector DNA from cells.

(2) Screening Using a Synthetic Oligonucleotide Probe

If all or part of the amino acid sequence of the desired protein has been elucidated (the sequence can be that in any region of the protein, provided that is specific and contains continuous amino acids), oligonucleotides corresponding thereto may be synthesized, and used as a probe (after labelling with $^{32}P$, $^{35}S$, biotin or the like), namely, hybridized with DNA from the transformant which has been immobilized on a nitrocellulose filter to select positive strains. As the probe, there can be used one oligonucleotide which is designed considering the frequency of codons in a host, or a mixture of possible oligonucleotides. In the latter case, the number of oligonucleotides to be used can be reduced by using inosine.

DNA thus obtained may be sequenced by, for example, the Maxam-Gilbert chemical modification technique [cf. Maxam, A. M. and Gilbert. W. (1980) in "Methods in Enzymology" 65, 499–576], the dideoxy chain termination method [cf. Messing J. and Vieira J. (1982) Gene, 19, 269–276] or the like.

In recent years, there has been widely used automated DNA sequencers using a fluorogenic dye, for example Sequence robot "CATALYST 800" and the model 373A DNA Sequencer, manufactured by Perkin-Elmer Japan, Inc.

By using systems such as those described above, determination of the DNA sequence can be performed efficiently and safely. Based on the data of the nucleotide sequences of the DNA of the present invention thus determined and the data of the N-terminal amino acid sequences of the heavy chain and the light chain thereof, the entire amino acid sequences of the heavy chain and the light chain of a monoclonal antibody of the present invention can be determined.

Construction of a mutant wherein one or more amino acids in an amino acid sequence is deleted may be performed, for example, by cassette mutagenesis [cf. Toshimitsu Kishimoto, "Shin-Seikagaku Jikken Kouza 2: Kakusan III Kumikae DNA Gijutsu", 242–251].

Such DNA sequences may be prepared by chemical synthesis using a conventional method, such as the phosphite triester method [cf. Hunkapiller, M., et al., (1984), Nature, 310, 105–111]. Codons for each amino acid themselves are known, and a specific codon for a desired amino acid may be selected arbitrarily, or by taking a frequency of a given codon in a host into account. Partial modification of the nucleotide sequence can be accomplished by conventional techniques, such as site-specific mutagenesis utilizing synthetic oligonucleotide primers encoding the desired modifications [cf. Mark, D. F., et al., (1984), Proc. Natl. Acad. Sci. USA, 81, 5662–5666].

Whether DNA can be hybridized with DNA encoding the light chain or the heavy chain of the anti-Fas monoclonal antibody that is preferable as an active ingredient in the pharmaceutical composition of the present invention can be determined, for example, by using a DNA probe labelled with $(\alpha-^{32}P)dCTP$ or the like, for example, by the random primer method [cf. Feinberg, A. P. and Vogelstein, B. (1983), Anal. Biochem., 132, 6–13], by the nick translation method [cf. Maniatis, T., et al., (1982), in "Molecular Cloning A Laboratory Manual", Cold Spring Harbor Laboratory, NY] or the like. A suitable technique is as follows.

First, the DNA to be determined is adsorbed onto a nitrocellulose membrane or a nylon membrane, for example, being subjected to alkaline treatment if necessary, and then being fixed on the membrane by heating or UV irradiation. The membrane is next immersed in prehybridisation solution containing 6×SSC (1×SSC is a solution of 0.15 M NaCl and 0.015 M tri-sodium citrate), 5% v/v Denhardt solution and 0.1% v/v sodium dodecyl sulfate (SDS), and incubated at 55° C. for 4 hours or more. Then, the probe previously prepared is added in similar prehybridisation solution to a final specific activity of $1\times10^6$ cpm/ml, followed by incubation at 60° C. overnight. Subsequently, the membrane is washed at room temperature by repeated washing with 6×SSC for 5 minutes and further with 2×SSC for 20 minutes, and is then subjected to autoradiography.

By using the above method, DNA hybridizable with the DNA encoding the heavy or light chain of the anti-Fas monoclonal antibody that is preferable as an active ingredient in the pharmaceutical composition of the present invention can be isolated from any cDNA library or genomic library [cf. Maniatis, T., et al., (1982), "Molecular Cloning A Laboratory Manual", Cold Spring Harbor Laboratory, NY].

Integration of DNA thus obtained into an expression vector allows transformation of prokaryotic or eukaryotic host cells, thereby allowing the DNA to be expressed in the host cell.

Suitable prokaryotic host cells include, for example, *Escherichia coli, Bacillus subtilis*, and the like. In order to express the gene of interest in such host cells, these host cells may be transformed with a plasmid vector containing a replicon derived from a species compatible with the host, namely an origin of replication and a promoter sequence, such as lac UV5. These vectors preferably have sequences capable of conferring a selection phenotype on the transformed cell. A suitable strain of *E. coli* is strain JM109 derived from *E. coli* K12. Suitable vectors include pBR322 and the pUC series plasmids, without being limited thereto. Other known strains and vectors can also be utilized. Suitable promoters include the tryptophan (trp) promoter, the lactose promoter (lac), the tryptophan lactose promoter (tac), the lipoprotein promoter (lpp), the lambda (λ) PL promoter derived from bacteriophage, and the polypeptide chain elongation factor Tu (tufb) promoter, without being limited thereto.

A preferred strain of *Bacillus subtilis* is strain 207-25, and a preferred vector is pTUB228 [cf. Ohmura, K., et al., (1984), J. Biochem., 95, 87–93], without being limited thereto. A suitable promoter is the regulatory sequence of the *Bacillus subtilis* α-amylase gene. If desired, the DNA sequence encoding the signal peptide sequence of α-amylase may be linked to the DNA of the present invention to enable extracellular secretion.

Eukaryotic hosts include cells from vertebrate and yeast species. An example of vertebrate cells used is the monkey COS-1 cell line [cf. Gluzman, Y., (1981), Cell, 23, 175–182]. Suitable yeast cell hosts include baker's yeast (*Saccharomyces cerevisiae*), methylotrophic yeast (*Pichia pastoris*) and fission yeast (*Schizosaccharomyces pombe*). The cells mentioned above are generally used as the host cell, but the host cell to be used is not limited thereto.

In general, the requirements for suitable expression vectors for vertebrate cells are that they comprise: a promoter, usually located upstream of the gene to be expressed; an RNA splicing site; a polyadenylation site; and a transcription termination sequence; and an origin of replication if necessary. A suitable plasmid is, for example, pSV2dhfr containing the SV40 early promoter [cf. Subramani, S., et. al. (1981), Mol. Cell. Bio., 1, 854–864], without being limited thereto.

Suitable expression vectors for yeasts contain, for example, the promoter of the alcohol dehydrogenase gene [cf. Bennetzen, J. L. and Hall, B. D., (1982), J. Biol. Chem., 257, 3018–3025) or the promoter of a galactose metabolic enzyme (for example, gal 10) [cf. Ichikawa, K., et. al. (1993), Biosci. Biotech. Biochem., 57, 1686–1690], without being limited thereto. If desired, the DNA sequence encoding the signal peptide sequence of a yeast gene may be linked to the DNA to be expressed in order to enable extracellular secretion.

When COS-1 cells are used as a host cell, expression vectors suitably comprise the SV40 replication origin, enabling autonomous replication, a transcription promoter, a transcription termination signal and an RNA splicing site. The said expression vectors can be used to transform the COS-1 cells by any suitable method, such as the DEAE-dextran method [cf. Luthman. H, and Magnusson. G. (1983), Nucleic Acids Res., 11, 1295–1308], the phosphate calcium-DNA co-precipitation method [cf. Graham, F. L. and Van der Eb, A. J., (1973), Virology, 52, 456–457] and the electric pulse electroporation method [cf. Neumann, E., et. al., (1982), EMBO J, 1, 841–845]. A desired transformant can be obtained by these methods.

Preferably, COS-1 cells are co-transfected with two expression vectors: one containing DNA encoding the heavy chain and the other containing DNA encoding the light chain, to provide a transformant producing the recombinant anti-Fas antibody. However, the method of producing the recombinant anti-Fas antibody is not limited thereto. For example, it is also possible to construct only one expression vector containing both the DNA encoding the heavy chain and the DNA encoding the light chain, which is expressed simultaneously, and to transfect COS-1 cells therewith.

Desired transformants obtained by the above methods may be cultured using conventional methods, the recombinant anti-Fas antibody being expressed either intra- or extra-cellularly. Suitable culture media include various commonly used media, depending on the host chosen. For example, suitable media for COS-1 cells include RPMI-1640 and Dulbecco's Modified Eagle Medium (DMEM), which can be supplemented with, as desired, fetal calf serum (FCS).

The culture temperature for culturing the transformant may be any suitable temperature which does not markedly depress the protein synthesis capability of the cell, and is preferably in the range of 32 to 42° C., most preferably 37° C. If desired, the culture may be effected in an atmosphere containing 1 to 10% (v/v) carbon dioxide.

The fraction containing the anti-Fas antibody protein produced intra- or extra-cellularly by the transformants as described above may be isolated and purified by various well known methods of separation according to the physical and chemical properties of the protein. Suitable specific methods of separation include: treatment with commonly used precipitating agents for protein; various methods of chromatography such as ultrafiltration, molecular sieve chromatography (gel filtration), adsorption chromatography, ion exchange chromatography, affinity chromatography and high performance liquid chromatography (HPLC), dialysis and combinations thereof.

According to the method described above, the highly pure recombinant, anti-Fas antibody can be readily produced in high yields.

In order to confirm that a recombinant anti-Fas antibody prepared by the above method specifically binds to Fas, an ELISA may be preferably performed in a manner similar to that described above for the evaluation of antibody titers in immunized mice.

On the other hand, a compound having a folate antagonist activity or a dihydrofolate reductase inhibiting activity, for example the compounds represented by the above formulae (I) to (XIX) can be produced according to the literature description referred to in the earlier explanation for each of the compounds. It is possible to determine whether other compounds have a folate antagonist activity or a dihydrofolate reductase inhibiting activity according to the methods for confirming a folate antagonist activity or a dihydrofolate reductase inhibiting activity, utilized in the literatures respectively.

The pharmaceutical composition of the present invention containing the above compounds as active ingredients can be used as an agent for prophylaxis and/or treatment of an autoimmune disease or rheumatoid arthritis in a mammal, for example, a human. Such a prophylactic or therapeutic agent may be administered in various forms. Examples of such forms include oral administration, with tablets, capsules, granules, powders, syrups or the like, or parenteral administration, with injection, dropping injection, suppositories or the like.

The amount of the anti-human Fas antibody and a dose of the compound having a folate antagonist activity or a dihydrofolate reductase inhibiting activity in the pharmaceutical composition of the present invention can vary depending on activity inherent in each antibody or each compound to be used. For example, when CH11 or HFE7A is used as the anti-human Fas antibody, and methotrexate is used as the compound having a folate antagonist activity or a dihydrofolate reductase inhibiting activity, it is preferable that the pharmaceutical composition of the present invention is prepared as a solution containing 0.1 to 100 mg/ml of CH11 or HFE7A and 0.05 to 5 nM of methotrexate, but the present invention is not limited thereto.

The dosage of the anti-human Fas antibody will be 0.001 to 10 mg/kg for a one time daily administration. The dosage of the compound having a folate antagonistic activity or a dihydrofolate reductase inhibiting activity will be 0.15 μg/kg to 0.15 mg/kg for a one time daily administration.

The dose will vary, depending on factors such as the condition, age and body weight of the patient, but usually it may be administered in an amount of from 0.1 mg to 1,000 mg at one time as the amount of anti-human Fas antibody by a subcutaneous, intramuscular or intravenous injection.

The efficacy for treatment of the autoimmune diseases or rheumatoid arthritis by using the pharmaceutical composition of the present invention prepared as described above can be checked by culturing cells (for example, human lymphocyte cell stock HPB-ALL (cf. Morikawa, S., et al. (1978) Int. J. Cancer 21, 166–170 to reference), Jurkat (American Type Culture No. TIB-152), synovial cells originating from the rheumatoid arthritis patient or the like) in a medium to which the pharmaceutical composition of the present invention is added, and measuring viability by methods such as MTT assay (cf. Green, L. M., et al. (1984) J. Immunological Methods 70, 257–268) or XTT assay indicated in the following examples. The pharmaceutical composition of the present invention can induce apoptosis in self-reactive lymphocytes which is one of the main causes of an autoimmune disease and in synovial cells proliferating abnormally in the rheumatoid arthritis affected part at a lower dose of anti Fas antibody, compared with the case where only an anti-Fas antibody is administered, and thus it is effective in treatment of these autoimmune diseases or rheumatoid arthritis. It has been reported also in European patent Application Laid-open publication No. 0909816 that the composition containing the anti-Fas antibody accepted to be effective in the experiments using the above-mentioned cultured cells is actually effective for treatment of autoimmune disease and rheumatoid arthritis with results of the experiment using the animal experiment model.

DETAILED DESCRIPTION OF THE INVENTION

The invention will now be illustrated in more detail with reference to the following Examples, but the present invention is not limited thereto.

EXAMPLE 1

The anti-human Fas monoclonal antibody HFE7A or CH11 (manufactured by Igaku seibutsugaku kenkyusho K.K.) described in European patent Application Publication No. 0909816 was used as an anti-Fas antibody.

Human lymphocyte cell stock HPB-ALL (cf. Morikawa, S., et al. (1978) Int. J. Cancer 21, 166–170) was cultured in RPMI 1640 medium containing 10% FCS (manufactured by Gibco B.R.L. Corporation) at 37° C., in the presence of 5% carbon dioxide gas for three days, and 50 μl of the culture ($2.5 \times 10^5$ cells/50 μl) were dispensed into each well of a 96-well microplate (manufactured by Sumitomo Bakelite Co., Ltd.). Then, 50 μl of the RPMI medium containing methotrexate (manufactured by Sigma Chemical Company), and an anti-Fas antibody (CH11 or HFE7A, 0.001 mg/ml solution was serially diluted by three times) were added to each well, and was cultured at 37° C.

The cells in the plate to which CH11 was added as an anti-Fas antibody were kept to be cultured at 37° C. overnight. On the other hand, the cells in the plate to which HFE7A was added were washed with the RPMI medium after being cultured for one hour, and then 100 μl/well of RPMI medium containing 1 μg/ml of anti-mouse IgG antibody (manufactured by Biosource corporation) were added. The cells were cultured at 37° C. for one hour, and then they were washed with serum-free RPMI medium. Subsequently, 100 μl/well of RPMI medium containing 0.05 nM of methotrexate were added thereto, and the cells were cultured at 37° C. overnight. Then, 50 μl of 25 μM PMS (phenazine methosulphate; Sigma Chemical Company), containing 1 mg/ml of XTT [2,3-bis(2-methoxy-4-nitro-5-sulphophenyl)-2H-tetrazolium-5-carboxyanilide zwitterion; Sigma Chemical Company] (final concentrations: 250 μg/ml as for XTT and 5 μM as for PMS) were added to each well. The plate was then incubated for 3 hours at 37° C., and the absorbance at 450 nm of each well was measured, to calculate cell viability, using the reducing power of the mitochondria as the index.

The viability of the cells in each well was calculated according to the following equation:

$$\text{viability } (\%) = 100 \times (a-b)/(c-b)$$

wherein "a" is the absorbance of a test well, "b" is the absorbance of a well with no cells and c is the absorbance of a well with no antibody added.

Figure 1:
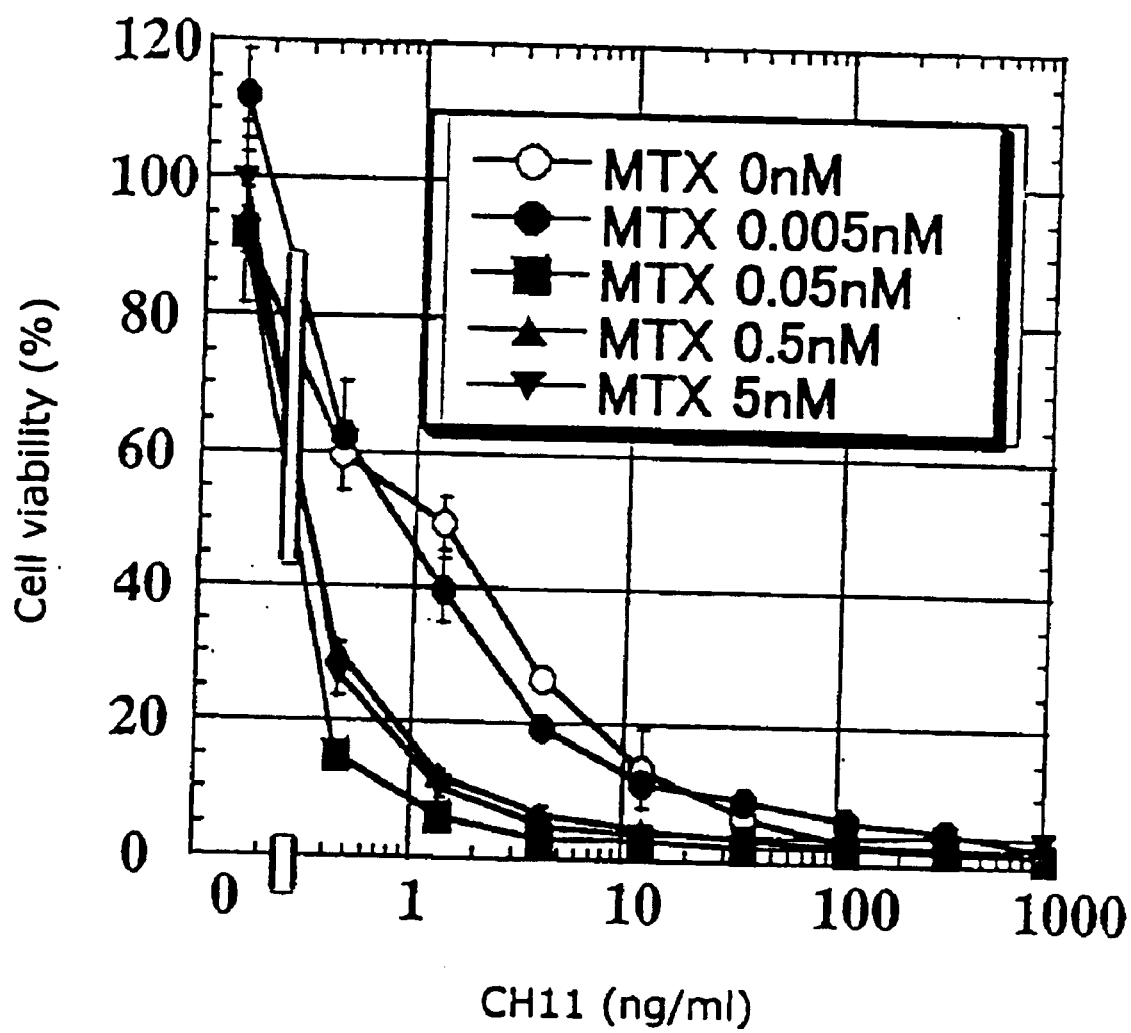
FIG. 1 is a graph showing a synergistic effect of anti-human Fas monoclonal antibody CH11 and methotrexate in inducing apoptosis in cells.
Figure 2:
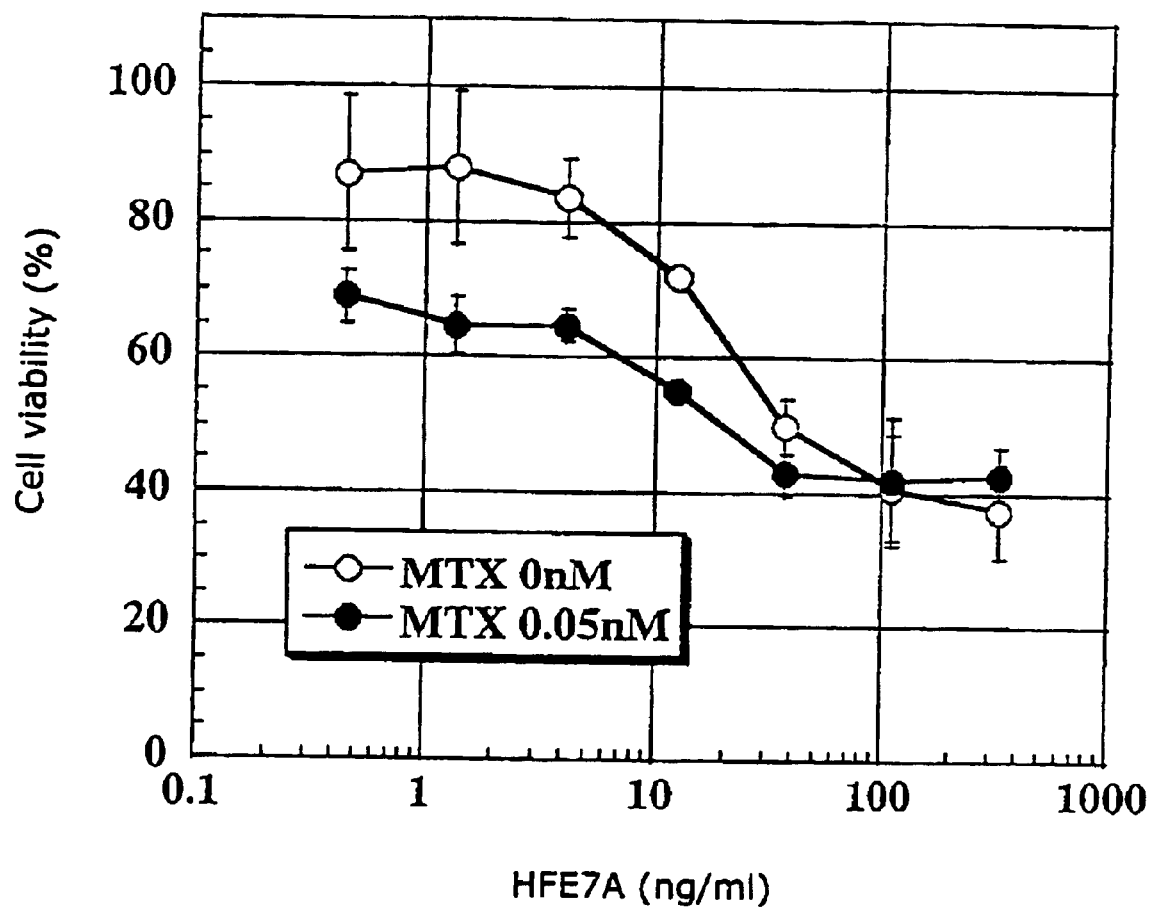
FIG. 2 is a graph showing a synergistic effect of anti-human Fas monoclonal antibody HFE7A and methotrexate in inducing apoptosis in cells.
Figure 3:
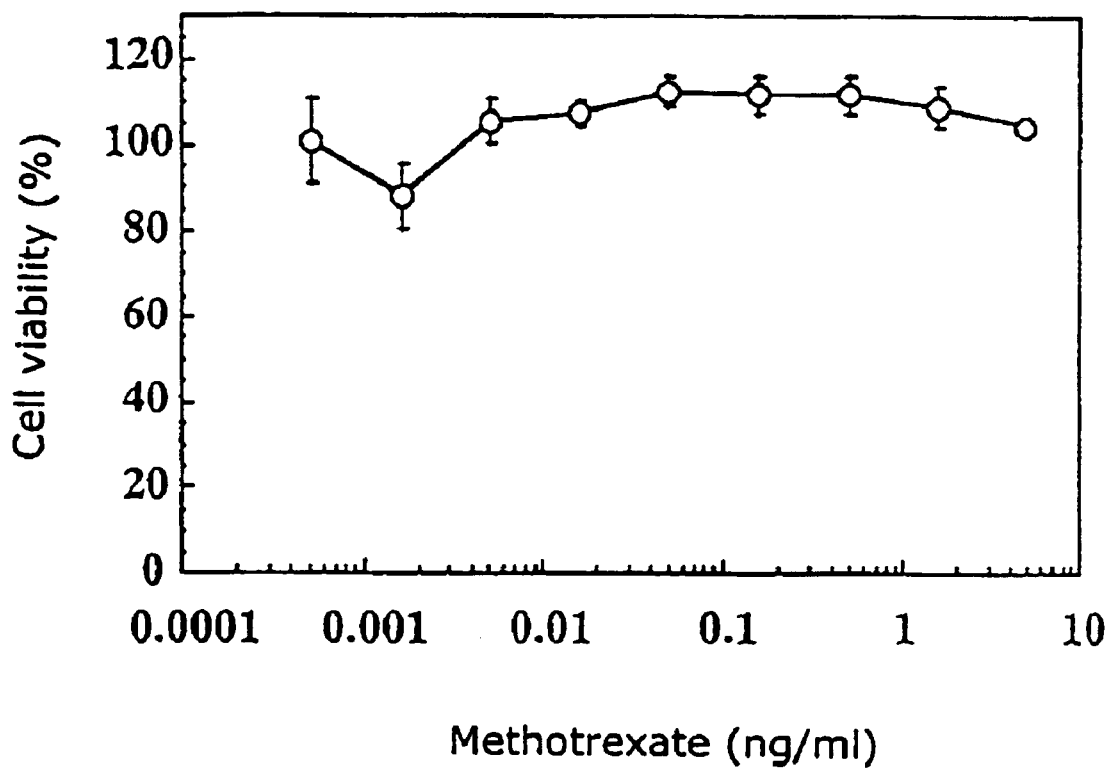
FIG. 3 is a graph showing cell viability in the presence of methotrexate.

As a result, it became clear that the apoptosis inducing activity of CH11 was significantly increased with addition of 0.05 nM or more of methotrexate (See FIG. 1. "MTX" in FIG. 1 represents methotrexate, hereinafter it represents the same). The apoptosis inducing activity of HFE7A was also increased with addition of 0.05 nM of methotrexate (See FIG. 2). When anti-Fas antibody was not added, but only methotrexate was added, there was almost no change in the viability of the cells (See FIG. 3). The dosage of the methotrexate is much lower than shown in a previous report [cf. McGahon A. J., et al. (1998) Br. J. Cancer 101, 539–547].

It was shown that the apoptosis inducing activity of the anti-Fas antibody was reinforced by addition of methotrexate, and the number of the cells that may cause an autoimmune disease can be reduced with a lower dose of an anti-Fas antibody, compared with conventional methods.

FORMULATION EXAMPLE

Therapeutic formulations of the anti-human Fas antibody and the compound having a folate antagonist activity or a dihydrofolate reductase inhibiting activity are prepared for storage by mixing the antibody having the desired degree of purity with optional physiologically acceptable carriers, excipients or stabilizers in the form of lyophilized formulations or aqueous solutions. Acceptable carriers, including excipients and stabilizers, are nontoxic to recipients at the dosages and concentrations employed, and include buffers such as phosphates, citrates, and other organic acids; antioxidants including ascorbic acid and methionine; preservatives (such as octadecyldimethylbenzyl ammonium chloride; hexamethonium chloride; benazalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or nonionic surfactants such as TWEEN™-80, or polyethylene glycol.

A pharmaceutical formulation for a sterile solution for use in the present invention, in addition to the active ingredients, may include the following:

0.01 M to 0.1 M phosphate buffer,
1 to 10 w/v % (or alternatively 5 to 10 w/v %) sucrose and 0.1 mg/ml TWEEN™-80.

A lyophilized powder of the above solution could be used.

The agent for prophylaxis and/or treatment of the present invention can be used in the form of an ampoule of a sterile solution or suspension which contains an anti-human Fas antibody and a compound having a folate antagonist activity or a dihydrofolate reductase inhibiting activity in water or in another pharmaceutically acceptable solution. Specifically, for example, 0.5 mg of anti-human Fas antibody and methotrexate (final concentration: 0.05 nM) are dissolved in 1 liter of water for injection, sterilely filled into an ampoule and sealed.

Alternatively, a sterile powder (preferably, prepared by lyophilization of the anti-human Fas antibody and compound having a folate antagonist activity or a dihydrofolate reductase inhibiting activity) may be filled into an ampoule, which may then be diluted with a pharmaceutically acceptable solution when it is used.

INDUSTRIAL APPLICABILITY

As described above, the present invention provides a novel pharmaceutical composition useful as an agent for prophylaxis and/or treatment of an autoimmune disease or rheumatoid arthritis. According to the present invention, the amount of the anti-Fas antibody to be used can reduced by using a compound having a folate antagonist activity or a dihydrofolate reductase inhibiting activity and an anti-human Fas antibody together. Thereby, the possibility that a patient becomes tolerant to an anti-Fas antibody as a result of production of antibodies against the anti-Fas antibody in the patient's body or the like can be decreased, and thus the pharmaceutical composition of the present invention is useful as an excellent agent for prophylaxis and/or treatment of an autoimmune disease or rheumatoid arthritis that can be used for a long time. Autoimmune diseases in the context of the present invention, include, but are not limited to, chronic thyroiditis, allergic encephalitis, myasthenia gravis, hyperthyroidism (Graves disease), extreme insulin resistance in diabetes, rheumatic fever, human hemolytic anemias, granulocytopenias, thrombocytopenias and systemic lupus erythematosis ("SLE").

What is claimed is:

1. A pharmaceutical composition comprising effective amounts of pharmacologically active agents, wherein said pharmacologically active agents comprise:
   (a) an anti-human Fas antibody having an apoptosis inducing activity, said anti-human Fas antibody being monoclonal antibody HFE7A or a humanized antibody of monoclonal antibody HFE7A; and
   (b) a compound having a folate antagonistic activity or a dihydrofolate reductase inhibiting activity, said compound being methotrexate,
   the relative amounts of said pharmacologically active agents (a) and (b) being such that said pharmacologically active agents (a) and (b) exhibit a synergistic apoptosis inducing activity.

2. The pharmaceutical composition according to claim 1, wherein said anti-human Fas antibody having apoptosis inducing activity is the monoclonal antibody HFE7A which is produced by a mouse-mouse hybridoma HFE7A, deposited as FERM-5828.

3. The pharmaceutical composition according to claim 1, wherein said anti-human Fas antibody having apoptosis inducing activity is a humanized antibody of the monoclonal antibody HFE7A which is produced by a mouse-mouse hybridoma HFE7A, deposited as FERM-5828.

4. A pharmaceutical composition in the form of a solution comprising effective amounts of pharmacologically active agents together with a diluent therefor, wherein said pharmacologically active agents comprise:
   (a) an anti-human Fas antibody having apoptosis inducing activity which is monoclonal antibody HFE7A, or a humanized antibody thereof in a concentration of 0.1 to 100 ng/ml; and
   (b) methotrexate in a concentration of 0.05 to 5 nM, the relative amounts of said active ingredients (a) and (b) being such that they exhibit a synergistic apoptosis inducing activity.

5. A method for the treatment of a disease selected from the group consisting of rheumatoid arthritis, chronic thyroiditis, allergic encephalitis, myasthenia gravis, hyperthyroidism, extreme insulin resistance in diabetes, rheumatic fever, human hemolytic anemias, granulocytopenias, thrombocytepenias and systemic lupus erythematosis comprising administering to a human in need thereof effective amounts of the following active ingredients:
   (a) an anti-human Fas antibody having an apoptosis inducing activity, said anti-human Fas antibody being monoclonal antibody HFE7A or a humanized antibody of monoclonal antibody HFE7A; and
   (b) a compound having a folate antagonistic activity or a dihydrofolate reductase inhibiting activity, said compound being methotrexate,
   the relative amounts of the active ingredients (a) and (b) being administered such that said active ingredients (a) and (b) exhibit a synergistic apoptosis inducing activity.

6. The method according to claim 5, wherein said anti-human Fas antibody having apoptosis inducing activity is the monoclonal antibody HFE7A which is produced by a mouse-mouse hybridoma HFE7A, deposited as FERM-5828.

7. The method according to claim 6, wherein said disease is rheumatoid arthritis.

8. The method according to claim 5, wherein the anti-human Fas antibody is administered in a daily dosage of 0.001 to 10 mg/kg and the compound having a folate antagonistic activity or a dihydrofolate reductase inhibiting activity is administered in a daily dosage of 0.15 µg/kg to 0.15 mg/kg.

9. The method according to claim 8, wherein said disease is rheumatoid arthritis.

10. The method according to claim 5, wherein said disease is rheumatoid arthritis.

11. The method according to claim 5, wherein said anti-human Fas antibody having apoptosis inducing activity is a humanized antibody of the monoclonal antibody HFE7A which is produced by a mouse-mouse hybridoma HFE7A, deposited as FERM-5828.

12. The method according to claim 11, wherein said disease is rheumatoid arthritis.

13. A method for the treatment of a disease selected from the group consisting of rheumatoid arthritis, chronic thyroiditis, allergic encephalitis, myasthenia gravis, hyperthyroidism, extreme insulin resistance in diabetes, rheumatic fever, human hemolytic anemias, granulocytopenias, thrombocytepenias and systemic lupus erythematosis comprising administering to a human in need thereof effective amounts of a medicament in the form of a solution comprising pharmacologically active agents together with a diluent therefor, wherein said pharmacologically active agents comprise:

(a) an anti-human Fas antibody having apoptosis inducing activity selected from the group consisting of monoclonal antibody HFE7A and a humanized antibody of monoclonal antibody HFE7A, in a concentration of 0.1 to 100 ng/ml; and (b) methotrexate at a concentration of 0.05 to 5 nM, the relative amounts of said pharmacologically active agents (a) and (b) being such that said pharmacologically active agents (a) and (b) exhibit a synergistic apoptosis inducing activity.

14. The method according to claim 13, wherein said disease is rheumatoid arthritis.

\* \* \* \* \*